United States Patent [19]

van der Vies

[11] 4,083,973
[45] Apr. 11, 1978

[54] PHARMACEUTICAL PREPARATION ADAPTED FOR ORAL ADMINISTRATION

[75] Inventor: Johannes van der Vies, Oss, Netherlands

[73] Assignee: Akzona Incorporated, Asheville, N.C.

[21] Appl. No.: 714,454

[22] Filed: Aug. 16, 1976

[30] Foreign Application Priority Data

Aug. 27, 1975 Netherlands .......................... 7510104

[51] Int. Cl.$^2$ ........................... A61K 31/56; C07J 1/00
[52] U.S. Cl. .................................... 424/239; 424/243; 260/397.3
[58] Field of Search ................ 424/240, 243; 260/397.4

[56] References Cited

U.S. PATENT DOCUMENTS 2,998,423  8/1961  De Wit et al. ..................... 260/397.4
3,016,388  1/1962  De Wit ............................... 260/397.4

OTHER PUBLICATIONS

Gould et al., Jour. Amer. Chem. Soc. (vol. 79) Aug. 20, 1957, pp. 4472–4475.
Dorfman et al., "Androgens," John Wiley and Sons, Inc., New York (1956) pp. 512 and 513.

Primary Examiner—Elbert L. Roberts
Attorney, Agent, or Firm—Stevens, Davis, Miller & Mosher

[57] ABSTRACT

The invention relates to a novel pharmaceutical preparation with anabolic activity adapted for oral administration comprising a nandrolone (= 19-nor-testosterone)-17$\beta$-ester, the ester group of which has been derived from aliphatic carboxylic acids having 9–18 carbon atoms, in combination with a non-steroidal lipoid. The preparation may additionally contain a mineralocorticoid steroid. The invention also relates to novel nandrolone-17$\beta$-esters.

31 Claims, No Drawings

PHARMACEUTICAL PREPARATION ADAPTED FOR ORAL ADMINISTRATION

The invention relates to a novel pharmaceutical preparation with anabolic activity adapted for oral administration, the said preparation containing a 17β-ester of nandrolone (= 19-nor-testosterone), and to methods for the preparation thereof. The invention also relates to novel 17β-esters of nandrolone.

Nandrolone and the 17β-esters thereof are known as substances with anabolic activity, possessing only slight androgenic activity in comparison with testosterone and the 17β-esters thereof. In particular, nandrolone-17β-esters derived from aliphatic carboxylic acids with 9-18 carbon atoms are potent anabolic agents. One of the best known nandrolone esters is nandrolone decanoate, which as an oily solution under the trade name Deca-Durabolin finds use in medicine as an injection preparation with a pronounced and protracted protein-sparing effect.

As already noted, the nandrolone-17β-esters are administered parenterally, predominantly by the intramuscular route. When given orally they are scarcely active, or in any case much less active. An advantage of parenteral administration is that a good effect can be achieved with a relatively low dosage. The use of 17β-esters results furthermore in a depot effect, so that an effective plasma nandrolone level is not only obtained rapidly after an intramuscular injection, but this nandrolone level may also persist for several weeks.

There are also objections to the parenteral form of administration. A patient is not usually capable of giving him- or herself an injection; for this, a doctor or a trained nurse is almost always necessary. Furthermore, repated parenteral administration may cause local reactions. A further disadvantage associated with the parenteral administration of long-acting preparations is that the action thereof cannot be interrupted or stopped. An oral administration form would therefore be far more preferable than a parenteral form.

Surprising, it has now been found that certain nandrolone esters, specifically the esters derived from aliphatic carboxylic acids with 9-18 carbon atoms, are orally active if they are administered in combination with a non-steroidal lipoid substance. This is the more surprising since the nandrolone-17β-esters derived from aliphatic carboxylic acids with less than 9 or more than 18 carbon atoms are distinctly less active orally under these conditions.

The invention therefore relates to a novel pharmaceutical preparation with anabolic activity adapted for oral administration, containing an ester of nandrolone, and is characterized by the incorporation into a pharmaceutical form suitable for oral administration of one or more nandrolone-17β-esters, derived from an aliphatic carboxylic acid with 9-18 carbon atoms, together with a pharmaceutically acceptable non-steroidal lipoid. The invention also encompasses the method for preparing said preparation.

The term "aliphatic carboxylic acid" also includes branched chain aliphatic and cycloaliphatic carboxylic acids.

In the preparation according to the invention, preferably one or more nandrolone esters derived from an aliphatic carboxylic acid with 10-16 carbon atoms are present. These esters have been shown to possess the highest activity, particularly the α- and β-methyl substituted aliphatic carboxylic acid esters.

As examples of aliphatic carboxylic acids with 9-18 carbon atoms, from which the nandrolone esters are derived, the following can be given: pelargonic acid, capric acid, undecanoic acid, lauric acid, tridecanoic acid, myristic acid, pentadecanoic acid, decenoic acid, undecenoic acid, palmitic acid, stearic acid and the branched-chain and cyclic analogues of these acids such as α-(and β-)methyl-caprylic acid, α-(and β-)methyl-pelargonic acid, α-(and β-)methyl-capric acid, β,β-dimethyl-pelargonic acid, β-(p-methyl-cyclohexyl)-propionic acid, β-(p-ethylcyclohexyl)-propionic acid, β-(cycloheptyl)-propionic acid, α-(and β-)methyl-β-cyclohexyl propionic acid, cyclododecyl-carboxylic acid, bicyclo[2,2,1]-heptyl-2'-carboxylic acid, adamantane carboxylic acid, adamantyl-acetic acid, 4'-methyl-bicyclo[2,2,2]-oct-2'-enyl carboxylic acid and β-(bicyclo[2,2,2]octyl)propionic acid. The nandrolon ester is preferably derived from capric acid, undecanoic acid, lauric acid, tridecanoic acid, myristic acid and more preferably from the α- or β-methyl-substituted and cyclic isomers of these acids.

Various of the nandrolone esters indicated above are novel compounds. The present invention therefore also comprises novel nandrolone esters with interesting anabolic properties, said novel nandrolone esters having the formula:

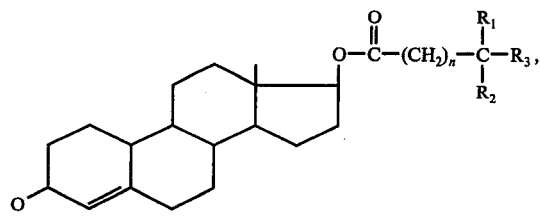

wherein $n = 0$ or 1 and preferably 0; $R_1$ = alkyl (1-10 C), preferably $CH_3$; $R_2$ = H or alkyl (1-10 C), preferably H; $R_3$ = an aliphatic group having 1-16 C-atoms, preferably 6-12 C-atoms, which group may contain one or more rings having 5-12 C-atoms, preferably 5-8 C-atoms, or $R_1$ and $R_3$ form together with the C-atom to which they are attached a cycloaliphatic group having 7-12 C-atoms, preferably 8-10 C-atoms, which cycloaliphatic group is or may be substituted by an aliphatic group having 1-6 C-atoms, with the proviso that the total number of C-atoms in the ester group is in the range of 9-18 C-atoms, preferably 9-16 C-atoms and still more preferably 10-14 C-atoms.

The novel esters can be prepared according to methods known in the art, for example by reacting nandrolone with the organic carboxylic acid or with a functional derivative thereof, such as the acid chloride or the acid anhydride, in a solvent and in the presence of a water-binding agent or a base, such as pyridine.

By pharmaceutically acceptable non-steroidal lipoids are meant plant and animal oils and fats consisting of the mono-, di- and triglycerides of various fatty acids or containing these as main constituents; fatty acid esters of alcohols; higher aliphatic alcohols; saturated and unsaturated fatty acids; the commercially available synthetic and semisynthetic mono-, di- and triglyceride oils and glycerol ethers; certain types of wax and mixtures of two or more of the above-noted substances. The lipoid substance is preferably liquid at normal temperature, that is, at a temperature in the range of about 10° C to about 35° C. The nandrolone ester is then dissolved in the lipoid substance and the solution is incorporated into a preparation or, as the case may be, converted into a pharmaceutical form. At normal temperature, part of the ester may be present in the liquid lipoid as a suspension, in which case the quantities of ester and lipoid substance are mutually adjusted in such a way that at body temperature the ester is completely dissolved in the lipoid substance. The intensification of the oral activity of the nandrolone esters according to the invention appears to be greatest when a lipoid substance liquid at normal temperature is used.

Examples of lipoid substances which may be used in the preparation according to the invention are: arachis oil, castor oil, sesame oil, linseed oil, soya bean oil, sunflower seed oil, olive oil, fish liver oil, ethyl oleate, oleyl oleate, glyceryl trioleate, glyceryl diolate, glyceryl monooleate, cetyl alcohol, stearyl alcohol, capric acid, undecenoic acid, undecanoic acid, lauric acid, oleic acid, synthetic glycerides of saturated fatty acids, with 8 to 10 or 12 carbon atoms such as the commercial products Syndermin GTC and Miglyol 812, polyoxyethylene derivatives of glycerol, such as the commercial product Labrafil 1944, bee's wax and mixtures of two or more of these substances.

The invention herein referred to provides an oral pharmaceutical preparation with anabolic activity. By incorporating an orally active mineralocorticoid into the preparation, the invention also offers the possibility of preparing an orally active pharmaceutical formulation which possesses mineralocorticoid properties in addition to anabolic properties.

Pharmaceutical preparations with both anabolic and mineralocorticoid actions, effective on subcutaneous administration, are known. As an example, the commercially available preparation Docabolin, for intramuscular injection, can be cited.

Such preparations, which in addition to powerful protein-sparing and roborant properties also have a normalizing effect on a reduced blood pressure, are used for various indications including hypotension, debilitating conditions, conditions associated with exhaustion, during convalescence, burns and infantile dystrophy.

As orally active mineralocorticoid, one or more esters of desoxycorticosterone are incorporated into the anabolic preparation according to the invention, such esters being preferably derived from an aliphatic carboxylic acid with 9–18 carbon atoms.

The desoxycorticosterone ester may be derived from the same aliphatic carboxylic acid as the nandrolone ester, and is preferably derived from the carboxylic acids with 10–12 carbon atoms.

The presence of the oily component results in a surprising intensification of the oral activity of the desoxycorticosterone ester.

The preparation according to the invention may be administered per os in various dosage forms, for example in the form of tablets, capsules, grains, pills, boli, dragees, powders, granulates, microcapsules or chewable tablets. In addition to the anabolic ester(s), the lipoid substance and optionally the mineralocorticoid compound, the dosage form may contain one or more of the usual excipients, for example benzyl alcohol to increase the solubility of the active agent in the oily component, water, thickening agents such as gelatine or agar-agar, polyethylene glycols, lactose, starch, talc or magnesium stearate. Other agents, such as preservatives, emulsifying agents, stabilizing agents, wetting agents, flavours, dyes, fillers, binding agents and/or coating agents may optionally be present.

The capsules may be soft or hard gelatine capsules, in which the active principle and the lipoid may be present in granular or finily divided intimate admixture or may be present in the form of an oily solution or suspension.

The combination of nandrolone-17$\beta$-ester and lipoid, when liquid or semi-liquid, may also be processed to solid oral formulations such as pills or tablets. For that purpose the oily solution of nandrolone-17$\beta$-ester is, for example, absorbed on calcium phosphate, lactose or cellulose derivatives and then processed to tablets or pills in the usual way. Combinations of nandrolone-17$\beta$-esters with lipoids, such as glycerylmono-oleate or capric acid, which are solid or semi-solid at room temperature, but are liquid at body temperature, may be granulated or processed to coated pills or tablets.

As already noted above, the nandrolone esters according to the invention are preferably administered dissolved in lipoid substances liquid at normal temperature, such as, for example, vegetable and animal oils, oleic acid, linoleic acid or undecanoic acid. When a mineralocorticoid is present, this is preferably also present dissolved in the oil, in addition to the nandrolone ester.

The most suitable oral administration form for this liquid form of the preparation according to the invention is the soft-shell gelatine capsule or microcapsule. In accordance with a method usual in the technique, the oily solution containing the active component(s) and optionally other ingredients is encapsulated to soft-shell gelatine capsules or microcapsules with the desired dimensions and containing the desired amount(s) of active substance(s). The microcapsules can also be processed to tablets or pills according to well-known pharmaceutical formulation methods.

The nandrolone-17$\beta$-ester(s) concentration in the preparation according to the invention can vary within considerable limits, on the understanding that the amount of nandrolone-17$\beta$-ester(s) by weight does not exceed the amount of lipoid substance by weight or in other words the nandrolone-17$\beta$-ester(s) concentration in the preparation is 50% by weight or less and is usually in the range of 1–25% by weight.

As indicated above, the amount of lipoid by weight in the preparation according to the invention is equal to or higher than the amount of nandrolone-17$\beta$-ester by weight. Depending on the other constituents present in the preparation (excipients, capsule, shell, coating) the amount of lipoid substance per dosage unit will vary from 5 to 95% by weight and is usually in the range of 20–80% by weight. The amount of nandrolone-17$\beta$-ester(s) per dosage unit, for example a capsule or a tablet, may also vary within wide limits, for example from 0.1 mg to 100 mg, and is preferably between 1 mg and 50 mg.

When the desoxycorticosterone ester is present in the preparation according to the invention, the amount thereof per dosage unit is within the range 0.5 to 50 mg, and the requirement, that the amount of desoxycorticosterone ester by weight does not exceed the amount of lipoid substance by weight, also applies.

The exceptional anabolic properties of the preparations according to the invention have been demonstrated in the known Hershberger test with castrated rats. A number of nandrolone-17$\beta$-esters were administered orally twice daily for 7 days as solutions in arachis oil. Nandrolone itself was also tested in this way.

With nandrolone, its lower esters such as acetate and propionate, and the nandrolone esters derived from aliphatic carboxylic acids with more than 18 carbon atoms, given in dosages of 2×2.0 mg/day, the weight of the M-levator ani was shown to increase by 40–60%, while with the esters derived from aliphatic carboxylic acids with 9–18 carbon atoms, such as the decanoate, the undecanoate, the dodecanoate, the tetradecanoate etc., the increase proved to be 100–150%, being therefore 2 – 3 times as great. For cyclic esters, for example adamantyl carboxylate, and for branched chain esters, for example α-methyl-decanoate, said increase is even more than 150%.

Experiments with other lipoid substances, such as sesame oil, soya bean oil, glyceryl trioleate, oleic acid and undecenoic acid, gave similar results. It was obvious that nandrolone-17β-esters derived from aliphatic carboxylic acids with more than 8 and less than 18 C-atoms, in the presence of a lipoid substance, are much more active on oral administration than the other esters, and that specifically the esters with 10–14 carbon atoms, particularly the branched chain isomers, are very active. In clinical studies a distinct protein-sparing effect was demonstrated when a daily dosage of 1–3 dosage units of an anabolic preparation according to the invention was given for a few weeks.

The invention is further illustrated by means of the following examples:

EXAMPLE I

Soft-shell gelatine capsules

A sterile solution of nandrolone-17β-undecanoate in arachis oil, containing 83.33 g per liter, was prepared, and this solution was encapsulated in soft-shell gelatine capsules, with due regard for aseptic precautions. The soft-shell gelatine capsules obtained had a content of 0.12 ml, so that the amount of active substance present was 10 mg per capsule. The capsule wall consisted of 68.1% gelatine, 15.5% glycerol, 13.7% sorbitol, 0.4% sodium ethyl/propyl p-hydroxybenzoate, 0.5% TiO$_2$ and 1.8% Cochineal Red (dye).

A number of nandrolone-17β-esters in various lipoid substances were processed in a similar way to give soft-shell capsules, for which details are given in table A.

Table A

| ester | lipid substance | capsule content | mg active substance capsule |
|---|---|---|---|
| -17β-undecanoate | oleic acid | 0.12 | 5 |
| -17β-decanoate | capric acid | 0.08 | 10 |
| -17β-undecanoate | undecenoic acid | 0.18 | 25 |
| -17β-undecanoate | soya bean oil | 0.12 | 10 |
| -17β-dodecanoate | ethyl oleate | 0.12 | 20 |
| -17β-tetradecanoate | linseed oil | 0.12 | 10 |
| -17β-α-methyl-decanoate | oleic acid | 0.08 | 5 |
| -17β-adamantyl-carboxylate | arachis oil | 0.12 | 5 |
| -17β-α-methyl-β-cyclohexylpropionate | linseed oil | 0.08 | 5 |

EXAMPLE II

| Tablets | | |
|---|---|---|
| Nandrolone-17β-undecanoate | 10.0 | mg |
| Capric acid | 20.0 | mg |
| Lactose | 140.0 | mg |
| Potato starch | 80.0 | mg |
| | 250.0 | mg |

Nandrolone-17β-undecanoate was dissolved with gentle warming in capric acid, after which the solution was homogenously absorbed in the lactose. After mixing with potato starch and a little water, the granulate thus obtained was dried. The dry granulate was tabletted in the usual way.

Tablets of the following compositions were prepared in a similar way:

| | | |
|---|---|---|
| Nandrolone-17β-α-methyldecanoate | 5.0 | mg |
| Glyceryl mono-oleate | 50.0 | mg |
| Lactose | 150.0 | mg |
| Potato starch | 95.0 | mg |
| | 300.0 | mg |
| Nandrolone-17β-dodecanoate | 10.0 | mg |
| Desoxycorticosterone undecanoate | 10.0 | mg |
| Stearyl alcohol/bee's wax | 20.0 | mg |
| Lactose | 130.0 | mg |
| Potato starch | 80.0 | mg |
| | 250.0 | mg |

EXAMPLE III

Hard-shell gelatine capsules

| | (a) | (b) |
|---|---|---|
| Nandrolone-17β-dodecanoate | 20.0 mg | 10.0 mg |
| Desoxycorticosterone dodecanoate | — | 10.0 mg |
| Lauric acid | 100.0 mg | 100.0 mg |
| Lactose | 130.0 mg | 130.0 mg |
| | 250.0 mg | 250.0 mg |

Nandrolone-17β-dodecanoate was dissolved in lauric acid at 50° C (in case (b) together with the desoxycorticosterone dodecanoate). The solution was homogenously absorbed in the lactose and the cooled solid mixture was powdered. Hard-shell gelatine capsules were filled with the finely-divided mixture (250 mg mixture per capsule).

EXAMPLE IV

Soft-shell gelatine capsules

Soft-shell gelatine capsules with contents as specified below were prepared in a way similar to that described in example I:

| a) | Nandrolone-17β-undecanoate | | 10.0 | mg |
|---|---|---|---|---|
| | Desoxycorticosterone decanoate | | 5.0 | mg |
| | Oleic acid | to | 0.18 | ml |
| b) | Nandrolone-17β-α-methyldecanoate | | 5.0 | mg |
| | Desoxycorticosterone decanoate | | 10.0 | mg |
| | Arachis oil | to | 0.24 | ml |

EXAMPLE V

Preparation of novel esters

To a solution of 5 g nandrolone in a mixture of 50 ml pentane and 5 ml pyridine were added dropwise in 1 hour 5 ml of α-methylcapric acid. The reaction mixture was stirred for 1 hour and then neutralized with an aqueous solution of sodiumbicarbonate, whereafter the organic layer was separated, washed with a solution of sodiumbicarbonate and with water till neutral. The organic layer was evaporated till dryness. The residue was chromatographed over a column of silicagel with toluene/acetone 9/1, yielding 6.3 g nandrolone-17β-α-methylcaprate, oil with $[\alpha]_D^{20} = +33°$ (in dioxane).

In a similar manner the following 17β-esters of nandrolone were prepared:

β-methyl-caprate
α,α-dimethylcaprate
α-methyl-β-cyclohexyl-propionate
β-cyclohexyl-butyrate
cyclo-octyl-carboxylate
β,β-diethyl-capronate
β-butyl-oenanthate
α-methyl-tridecylate
β,β-dimethyl-pelargonate
bicyclo[2,2,1]-heptyl-2'-carboxylate
bicyclo[2,2,1]-heptyl-2'-acetate

I claim:

1. A pharmaceutical composition with anabolic activity adapted for oral administration comprising
   at least one 17β-ester of nandrolone, the ester group thereof having been derived from an aliphatic carboxylic acid having 9 to 18 carbon atoms and
   a pharmaceutically acceptable non-steroidal lipoid carrier, in unit dosage form comprising per dosage unit, an anabolically effective amount of said ester in the range of from about 0.1 to about 100 mg., said ester constituting up to 50% by weight of said composition and said non-steroidal lipoid carrier being present in an amount at least equal to the amount of said ester.

2. The pharmaceutical composition of claim 1 wherein said ester has been derived from an aliphatic carboxylic acid having 10 to 14 carbon atoms.

3. The pharmaceutial composition of claim 1 wherein said non-steroidal lipoid carrier is liquid at room temperature.

4. The pharmaceutical composition of claim 1 wherein said ester is present in an amount of about 1 to about 25% by weight of said composition.

5. The pharmaceutical composition of claim 1 wherein said non-steroidal lipoid carrier constitutes 5 to 95% by weight of said composition.

6. The pharmaceutical composition of claim 5 wherein said non-steroidal lipoid carrier constitutes 20 to 80% by weight of said composition.

7. The pharmaceutical composition of claim 1 wherein said unit dosage form consists of a soft gelatin capsule containing a solution of said ester of nandrolone in said non-steroidal lipoid carrier.

8. The pharmaceutical composition of claim 1 wherein said non-steroid lipoid carrier is selected from the group consisting of arachis oil, castor oil, sesame oil, linseed oil, soya bean oil, sunflower seed oil, olive oil, fish liver oil, ethyl oleate, oleyl oleate, glyceryl trioleate, glyceryl dioleate, glyceryl monooleate, cetyl alcohol, stearyl alcohol, capric acid, undecenoic acid, undecanoic acid, lauric acid, oleic acid, synthetic glycerides of saturated fatty acids with 8 to 12 carbon atoms, polyoxyethylene derivatives of glycerol, bees' wax, and mixtures thereof.

9. The pharmaceutical composition of claim 1 wherein said ester is nandrolone-17β-undecanoate.

10. The pharmaceutical composition of claim 1 wherein said ester is nandrolone-17β-decanoate.

11. The pharmaceutical composition of claim 1 wherein said ester is nandrolone-17β-dodecanoate.

12. The pharmaceutical composition of claim 1 wherein said ester is nandrolone-17β-tetradecanoate.

13. The pharmaceutical composition of claim 1 wherein said ester is nandrolone-17β-α-methyl-decanoate.

14. The pharmaceutical composition of claim 1 wherein said ester is nandrolone-17β-adamantyl-carboxylate.

15. The pharmaceutical composition of claim 1 wherein said ester is nandrolone-17β-α-methyl-β-cyclohexylpropionate.

16. The pharmaceutical composition of claim 1 wherein said ester is nandrolone-17β-α-methylcaprate.

17. The pharmaceutical composition of claim 1 wherein said ester is nandrolone-17β-β-methyl-caprate.

18. The pharmaceutical composition of claim 1 wherein said ester is nandrolone-17β-α,α-dimethylcaprate.

19. The pharmaceutical composition of claim 1 wherein said ester is nandrolone-17β-α-methyl-β-cyclohexyl propionate.

20. The pharmaceutical composition of claim 1 wherein said ester is nandrolone-17β-β-cyclohexyl-butyrate.

21. The pharmaceutical composition of claim 1 wherein said ester is nandrolone-17β-cyclo-octyl-carboxylate.

22. The pharmaceutical composition of claim 1 wherein said ester is nandrolone-17β-β,β-diethyl-capronate.

23. The pharmaceutical composition of claim 1 wherein said ester is nandrolone-17β-β-butyl-oenanthate.

24. The pharmaceutical composition of claim 1 wherein said ester is nandrolone-17β-α-methyl-tridecylate.

25. The pharmaceutical composition of claim 1 wherein said ester is nandrolone-17β-β,β-dimethyl-pelagonate.

26. The pharmaceutical composition of claim 1 wherein said ester is nandrolone-17β-bicyclo-[2,2,1]-heptyl-2'-carboxylate.

27. The pharmaceutical preparation of claim 1 wherein said ester is nandrolone-17β-bicyclo[2,2,1]-heptyl-2'-acetate.

28. The pharmaceutical composition of claim 1 further comprising an orally active mineralocorticoid.

29. The pharmaceutical composition of claim 28 wherein said orally active mineralocorticoid is an ester of desoxycorticosterone, the ester group thereof having been derived from an aliphatic carboxylic acid having 9 to 16 carbon atoms.

30. A process for conducting protein-sparing therapy in a patient requiring such therapy comprising
    orally administering daily to said patient the pharmaceutical composition of claim 1.

31. A 17β-ester of nandrolone of the formula:

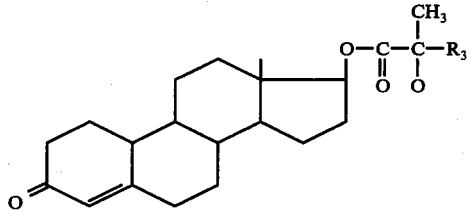

wherein $R_3$ is an aliphatic group having 7 to 11 carbon atoms.